United States Patent
Guo et al.

(10) Patent No.: US 10,214,755 B2
(45) Date of Patent: Feb. 26, 2019

(54) METHOD FOR PREPARING MERCAPTO FUNCTIONAL POLYESTER POLYOLS

(71) Applicant: NANJING TECH UNIVERSITY, Nanjing (CN)

(72) Inventors: Kai Guo, Nanjing (CN); Weijun Huang, Nanjing (CN); Ning Zhu, Nanjing (CN); Xin Hu, Nanjing (CN); Zheng Fang, Nanjing (CN); Yihuan Liu, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 0 days.

(21) Appl. No.: 15/352,849

(22) Filed: Nov. 16, 2016

(65) Prior Publication Data

US 2017/0073709 A1   Mar. 16, 2017

(30) Foreign Application Priority Data

May 6, 2016   (CN) .......................... 2016 1 0296658

(51) Int. Cl.
| | |
|---|---|
| *C12M 1/40* | (2006.01) |
| *C12M 3/06* | (2006.01) |
| *C12N 9/20* | (2006.01) |
| *C12P 7/62* | (2006.01) |
| *C08G 63/78* | (2006.01) |
| *C08G 63/82* | (2006.01) |
| *C12N 11/00* | (2006.01) |
| *C08G 63/688* | (2006.01) |

(52) U.S. Cl.
CPC .......... *C12P 7/625* (2013.01); *C08G 63/6882* (2013.01); *C08G 63/785* (2013.01); *C08G 63/823* (2013.01); *C12N 9/20* (2013.01); *C12N 11/00* (2013.01); *C12Y 301/01003* (2013.01); *C12M 21/18* (2013.01); *C12M 23/16* (2013.01); *Y02P 20/588* (2015.11)

(58) Field of Classification Search
CPC combination set(s) only.
See application file for complete search history.

(56) References Cited

PUBLICATIONS

Ning Zhu Highly chemoselective lipase from *Candida* sp. 99-125 catalyzed ring-opening polymerization for direct synthesis of thiol-terminated Poly(e-caprolactone) Chinese Chemical Letters 26 (2015) 361-364 (Year: 2015).*

Shuhei Namekawa, Enzymatic Synthesis of Polyesters from Lactones, Dicarboxylic Acid Divinyl Esters, and Glycols through Combination of Ring-Opening Polymerization and Polycondensation Biomacromolecules 2000, 1, 335-338 (Year: 2000).*

Yuya Asanomi Enzyme-Immobilized Microfluidic Process Reactors Molecules 2011, 16, 6041-6059.*

* cited by examiner

*Primary Examiner* — Kagnew H Gebreyesus
(74) *Attorney, Agent, or Firm* — CBM Patent Consulting, LLC

(57) ABSTRACT

A method to prepare functional polyester polyols by using micro-reaction device, wherein mixing ε-caprolactone/δ-valerolactone monomer with mercapto alcohol evenly with appropriate organic solution under moistureless conditions, and continuously transferring the prepared mixing solution into a micro-reaction device supported with an immobilized enzyme for polymerization to synthetize a poly (ε-caprolactone/δ-valerolactone). Compared with the prior art, the present invention achieves a continuous production by using immobilized lipase Novozyme435 as a catalyst.

8 Claims, 2 Drawing Sheets

METHOD FOR PREPARING MERCAPTO FUNCTIONAL POLYESTER POLYOLS

This application claims priority to Chinese Patent Application Ser. No. CN201610296658.0 filed on 6 May 2016.

TECHNICAL FILED

The present invention belongs to the field of high polymer chemistry, specifically relates to a method to prepare functional polyester polyols by using the micro-reaction device.

BACKGROUND

Poly (ε-caprolactone) (PCL) is a semi-crystalline polymer with melting point of 59~64° C., has advantageous biocompatibility and biodegradability and is widely applied in the biomedical and medicine control fields, such as being prepared into the bandage, the suture, the drug sustained release formulation etc. In addition, due to its special properties, the mercapto-functionalized poly(ε-caprolactone) (PCLSH) also has great potential for development and hence has a wide range of applications in areas such as click chemistry, nanomaterials and biomedical sciences.

The mercapto functional poly (ε-caprolactone) is mainly synthetized by the organic catalytic method, the metal catalytic method and enzyme catalysis method. In the present study, since the thiol group itself is relatively active, it requires to be protected and deprotected during the reaction, so that the operation step becomes too cumbersome. Meanwhile, since the acid or metal catalyst used in the reaction may remain in the product, the organic catalysis and metal catalysis methods not only affect the progress of the reaction, reduces the performance of product, but limits its application in the biomedical field due to the potential toxicity herein. However, the enzyme catalysis is observed by more and more researchers due to the advantages such as mild reaction condition, high efficiency, without metal residue etc. Currently, there are various free lipases, such as porcine pancreatic lipase, *pseudomonas* fluorescein lipase etc., which are to be used to catalyze the ring opening polymerization of the ε-caprolactone. Compared with these traditional free enzymes, the immobilized enzymes are increasingly being used as enzyme catalyzed polymerization due to their higher stability, catalytic activity, thiol group selectivity and recyclability.

However, most of current studies on enzyme-catalyzed employ a closed reaction vessel for batch reaction, and complex separation and purification processes are required after each batch of reaction. And in the reactor, generally, the reaction solution is sufficiently contacted with the enzyme by shaking or stirring. The shear forces generated during this process can cause the immobilized enzyme to rupture or even inactivate the enzyme, so that the stability and recyclabilty of the enzyme is reduced.

Due to their good properties in mixing and heat transferring, microchannel reactors have been used in polymerization reactions in recent years and have shown great potential. Compared to conventional tank reactor, the microreactor system is relatively and is not susceptible to water, air, and other factors so as to reduce some of cumbersome measures for removing impurities. And combining an immobilized enzyme catalytic method and a micro-channel reactor to synthesize a thiol-functionalized poly(ε-caprolactone) in one step in the present invention has advantages of a simplifying process, being easy to control the reaction process, being able to control the molecular weight, green, safety, a efficiency, a fast reaction, while having a high thiol group selectivity, and a good recyclability for the immobilized enzyme.

SUMMARY

The technical problem to be solved by the present invention is to provide a method to prepare the functional polyester polyols by using the micro-reaction device for solving the problem of lower conversion rate and lower selectivity for mercapto etc. existed in the prior art.

To solve above technical problems, the technical solution is employed in the present invention as follows:

A method to prepare a functional polyester polyols by using the micro-reaction device comprises the steps as follows:

(1) dissolving a lactone monomer into the organic solution;

(2) dissolving a mercapto alcohol into the organic solution;

(3) pumping a mixed system acquired from the step (1) and the step (2) after mixing homogeneously into a micro reactor in a micro-reaction device, a production may be obtained through separation and purification after sufficient reaction; wherein, the micro reactor is supported with the immobilized enzyme.

Wherein, all the vessels employed in the present invention are dewatered under a high temperature of 500° for three times, in which using argon for gas exchange per times; all the organic solvents employed in the present invention are treated anhydrously by means of the re-steam anhydrous method etc.

In step (1), the lactone monomer is ε-caprolactone or δ-valerolactone, the organic solution is toluene, tetrahydrofuran or dichloromethane; wherein, the concentration of the lactone monomer in the mixed system acquired in step (1) is 1-6 mol/L.

In step (2), the mercapto alcohol is 2-mercaptoethanol, 3-mercapto-1-propanol, 4-mercapto-1-butanol or 6-mercapto-1-hexanol, the organic solution is toluene, tetrahydrofuran or dichloromethane; wherein, the concentration of the mercapto alcohol in the mixed system acquired in step (2) is 0.01-0.6 mol/L.

Wherein, the organic solvent employed in step (1) and (2) may be either same or different.

In step (3), the reaction temperature in the micro reactor is 40-140° C., and the duration of stay is 1-180 mins.

In step (3), the immobilized enzyme is immobilized lipase Novozyme435.

In step (3), the method for separation and purification is: adding methanol into the product acquired from the reaction, and precipitating them under the condition of −40~−20° C., then vacuum drying the solid portion obtained by filtering to acquire the product; wherein, the volume of the methanol is 30~100 times the volume of the production solution.

Wherein, the molar ratio of the lactone monomer and the mercapto alcohol is 5~100:1.

Wherein, the mass ratio of the immobilized enzyme and the lactone monomer is 1:3~20.

Wherein, the micro-reaction device comprises a feed inlet, a micro mixer and a micro reactor connected in turn via a connecting pipe.

Wherein, an absorbent cotton in both ends and an immobilized enzyme section in the intermediate are included in the micro reactor. Arranging the absorbent cotton on both ends is for securing the position of the lipase in the enzyme tube to prevent the movement of the immobilized enzyme particles, while the immobilized enzyme is used for catalyzing polymerization.

Beneficial Effects

Compared with the prior art, the present invention has the advantages as follows:

The present invention utilizing the method of using the immobilized enzyme as catalysis avoids the residue of acids and metal catalysis in the product. Meanwhile, the micro reactor with immobilized enzyme greatly improves the stability of the enzyme, reduces the reaction time, achieves a continuous production. This method has such advantages as: a mild reaction condition, environmental friendly, a high efficiency, a low energy consumption, a high production, and a fast reaction speed, a high selectivity for sulfydryl, a good cyclic utilization of the immobilized enzyme.

DETAILED DESCRIPTION OF THE EMBODIMENTS

The present invention may be better understood according to the embodiments described below. However, it is easily understood for those skilled in the art that description of the embodiment is only for describing the present invention, but should not and will not be a limitation for the present invention as described in detail in claims.

Figure 1:
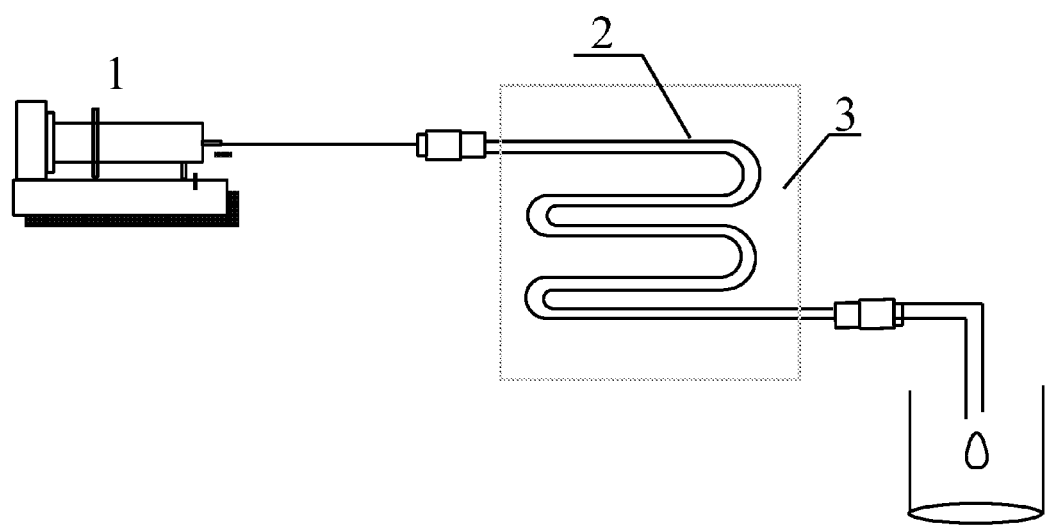
FIG. 1 is a schematic diagram of the micro reactor employed in the present invention.

In the embodiment of the present invention described below, as shown in FIG. 1, the configuration of the micro reactor includes a feed inlet1, a micro reactor2, a heater3. The operation step is: inputting continuously the mixed solution into micro reactor2 supported with the immobilized enzyme through feed inlet1 for reaction. Wherein, filling the immobilized lipase in the middle of the immobilized enzyme reaction channel with thin absorbent cotton is for catalyzing polymerization. The inside diameter of the micro reaction channel is 3.8 mm, the length of it is 300 mm. The immobilized enzyme therein selects *Candida antarctica* Lipase B (Novozyme435).

In the embodiment of the present invention described below, the detection method detecting the molecular weight of the production and the molecular weight distribution is employed as follows:

Employing Wyatt size exclusion chromatography system to formulate GPC column detection with SSI1500 pump, Wyatt Optilab rEX detector and Waters Styragel HR;

analytical conditions: the mobile phase is tetrahydrofuran, the flow rate is 0.7 mL/min, the column temperature is 25° C., the injection volume is 0.4 ml, sample preparation: 30 mg of the production diluted by tetrahydrofuran solution to 3 ml is injected after being filtered by a disposable filter (0.22 um organic filter membrane is included).

In the embodiment of the present invention described below, the conversion rate shows the percentage of a monomer mass reacted away in the total monomer mass, which may be calculated as follows:

$$C=(m_a/m_o)\times 100\%$$

Wherein, C represents for the conversion rate of a monomer; $m_a$ represents for the monomer mass reacted away; $m_o$ represents for the total monomer mass.

Embodiment 1. Employing the Immobilized Enzyme Micro Reactor for Synthetizing Mercapto Functional Poly (ε-Caprolactone)

Filling 1.18 g immobilized enzyme Novozyme435 into the micro channel, which is rinsed by the toluene after re-steaming dehydration to remove the air and water in the device. Adding 4.5656 g ε-caprolactone, 0.1790 g 6-mercapto-1-hexanol and 5.385 ml toluene solution into an ampoule bottle after dehydration under 500° C. high temperature and air exchanging for three times, transferring into a injector after shaking evenly, controlling the flow rate as 0.362 mL/min (reaction time as 5 mins), then inputting the mixed solution into the immobilized enzyme micro reaction channel for polymerization under 60° C., a poly (ε-caprolactone) reaction solution of 8 mins (about 2 ml) is collected after stable reaction of 14 mins. Adding 80 ml methanol and putting into a refrigerator with −30° C. for 4 h, then collecting the precipitation by filtering and putting into a vacuum drying chamber for 24 h after natural-air drying the precipitation, and a purified poly (ε-caprolactone) may be obtained. Through analytic determination of the production, the molecule weight is 3479 g/mol, the molecule weight distribution is 1.08, the conversion rate is 96%, the selectivity for sulfydryl is 91%. Compared with traditional autoclave reactor, using this immobilized enzyme micro reactor for synthetizing the poly (ε-caprolactone) improves greatly the reaction rate and reduces the reaction time. And the obtained molecule weight of polymer is controllable, the input reaction ratio is highly consistent, the molecule weight distribution is lower, the monomer conversion rate is higher, and the selectivity for sulfydryl is higher.

Embodiment 2. Employing the Immobilized Enzyme Micro Reactor for Synthetizing the Mercapto Functional Poly (ε-Caprolactone)

Filling 1.18 g immobilized enzyme Novozyme435 into the micro channel, which is rinsed by the toluene after re-steaming dehydration to remove the air and water in the device. Adding 11.414 g ε-caprolactone, 0.4475 g 6-mercapto-1-hexanol and 13.46 ml toluene solution into an ampoule bottle after dehydration under 500° high temperature and air exchanging for three times, transferring into a injector after shaking evenly, controlling the flow rate as 0.3017 mL/min, then inputting the mixed solution into the immobilized enzyme micro reaction channel for polymerization under 40°, −80°, a poly (ε-caprolactone) reaction solution of 7 mins (about 2 ml) is collected after stable reaction of about 17 mins each time. Adding 80 ml methanol and putting into a refrigerator with −30° C. for 4 h, then collecting the precipitation by filtering and putting into a vacuum drying chamber for 24 h after natural-air drying the precipitation, and a purified poly (δ-valerolactone) may be obtained. Through analytic determination of the product, the molecule weight are 3226 g/mol, 3300 g/mol, the molecule weight distribution are 1.128, 1.115, the conversion rate is 92%, the selectivity for sulfydryl are 92%, 93%.

Embodiment 3. Employing the Immobilized Enzyme Micro Reactor for Synthetizing the Mercapto Functional Poly (ε-Caprolactone)

Filling 1.18 g immobilized enzyme Novozyme435 into the micro channel, which is rinsed by the toluene after re-steaming dehydration to remove the air and water in the device. Adding 4.5656 g ε-caprolactone, 0.5379 g/0.1074 g/0.06712 g/0.05370 g 6-mercapto-1-hexanol and 5.3 ml toluene solution into an ampoule bottle after dehydration under 500° high temperature and air exchanging for three times, transferring into a injector after shaking evenly, controlling the flow rate as 0.6033 mL/min, 0.0362 mL/min, 0.03017 mL/min, 0.01508 mL/min respectively, then inputting the mixed solution into the immobilized enzyme micro reaction channel for polymerization under 60°, a poly (ε-caprolactone) reaction solution of 2 ml is collected after stable reaction (reaction solution of about 5 ml is discarded). Adding 80 ml methanol and putting into a refrigerator with −30° C. for 4 h, then collecting the precipitation by filtering and putting into a vacuum drying chamber for 24 h after natural-air drying the precipitation, and a purified poly (δ-valerolactone) may be obtained. Through analytic determination of the product, the molecule weight are 1200 g/mol, 5718 g/mol, 9112 g/mol, 9980 g/mol, the molecule weight distribution are 1.210, 1.225, 1.167, 1.195, the conversion rate are 94%, 95%, 93%, 92%, the selectivity for sulfydryl are 91%, 93%, 93%, 92%.

Embodiment 4. Employing the Immobilized Enzyme Micro Reactor for Synthetizing the Mercapto Functional Poly (ε-Caprolactone)

Filling 1.18 g immobilized enzyme Novozyme435 into the micro channel, which is rinsed by the toluene after re-steaming dehydration to remove the air and water in the device. Adding 4.5656 g ε-caprolactone, 0.1790 g 6-mercapto-1-hexanol and 5.3 ml tetrahydrofuran/dichloromethane solvent into an ampoule bottle after dehydration under 500° C. high temperature and air exchanging for three times, transferring into a injector after shaking evenly, controlling the flow rate as 0.362 mL/min, then inputting the mixed solution into the immobilized enzyme micro reaction channel for polymerization under 60°, a poly (ε-caprolactone) reaction solution of 2 ml is collected after stable reaction (reaction solution of about 5 ml is discarded). Adding 80 ml methanol and putting into a refrigerator with −30° C. for 4 h, then collecting the precipitation by filtering and putting into a vacuum drying chamber for 24 h after natural-air drying the precipitation, and a purified poly (ε-caprolactone) may be obtained. Through analytic determination of the product, the molecule weight are 3500 g/mol, 3480 g/mol, the molecule weight distribution are 1.103, 1.079, the conversion rate are 94%, 92%, the selectivity for sulfydryl are 92%, 94%.

Embodiment 5. Employing the Immobilized Enzyme Micro Reactor for Synthetizing the Mercapto Functional Poly (ε-Caprolactone)

Filling 1.18 g immobilized enzyme Novozyme435 into the micro channel, which is rinsed by the toluene after re-steaming dehydration to remove the air and water in the device. Adding 4.5656 g ε-caprolactone, 0.1042 g 2-mercaptoethanol/0.1228 g 3-mercapto-1-propanol/0.1415 g 4-mercapto-1-butanol and 5.3 ml toluene solvent into an ampoule bottle after dehydration under 500° C. high temperature and air exchanging for three times, transferring into a injector after shaking evenly, controlling the flow rate as 0.362 mL/min, then inputting the mixed solution into the immobilized enzyme micro reaction channel for polymerization under 60° C. a poly (ε-caprolactone) reaction solution of 2 ml is collected after stable reaction (reaction solution of about 5 ml is discarded). Adding 80 ml methanol and putting into a refrigerator with −30° C. for 4 h, then collecting the precipitation by filtering and putting into a vacuum drying chamber for 24 h after natural-air drying the precipitation, and a purified poly (ε-caprolactone) may be obtained. Through analytic determination of the product, the molecule weight are 3520 g/mol, 3580 g/mol, 3548 g/mol, the molecule weight distribution are 1.108, 1.120, 1.175, the conversion rate are 94%, 93%, 92%, the selectivity for sulfydryl are 96%, 95%, 95%.

Embodiment 6. Employing the Immobilized Enzyme Micro Reactor for Synthetizing the Mercapto Functional Poly (δ-Valerolactone)

Filling 1.18 g immobilized enzyme Novozyme435 into the micro channel, which is rinsed by the toluene after re-steaming dehydration to remove the air and water in the device. Adding 6.0072 g δ-valerolactone, 0.2685 g 6-mercapto-1-hexanol and 9.29 ml toluene solution into an ampoule bottle after dehydration under 500° C. high temperature and air exchanging for three times, transferring into a injector after shaking evenly, controlling the flow rate as 0.362 mL/min, then inputting the mixed solution into the immobilized enzyme micro reaction channel for polymerization under 60° C., a poly (δ-valerolactone) reaction solution of 8 mins (about 2 ml) is collected after stable reaction of 14 mins. Adding 80 ml methanol and putting into a refrigerator with −30° C. for 4 h, then collecting the precipitation by filtering and putting into a vacuum drying chamber for 24 h after natural-air drying the precipitation, and a purified poly (δ-valerolactone) may be obtained. Through analytic determination of the product, the molecule weight is 3100 g/mol, the molecule weight distribution is 1.161, the conversion rate is 93%, the selectivity for sulfydryl is 98%.

Embodiment 7. Employing the Immobilized Enzyme Micro Reactor for Synthetizing the Mercapto Functional Poly (δ-Valerolactone)

Filling 1.18 g immobilized enzyme Novozyme435 into the micro channel, which is rinsed by the toluene after re-steaming dehydration to remove the air and water in the device. Adding 11.414 g ε-caprolactone, 0.4475 g 6-mercapto-1-hexanol and 13.46 ml toluene solution into an ampoule bottle after dehydration under 500° high temperature and air exchanging for three times, transferring into a injector after shaking evenly, controlling the flow rate as 0.3017 mL/min, then inputting the mixed solution into the immobilized enzyme micro reaction channel for polymerization under 40°, 80°, a poly (ε-caprolactone) reaction solution of 7 mins (about 2 ml) is collected after stable reaction of about 17 mins each time. Adding 80 ml methanol and putting into a refrigerator with −30° C. for 4 h, then collecting the precipitation by filtering and putting into a vacuum drying chamber for 24 h after natural-air drying the precipitation, and a purified poly (δ-valerolactone) may be obtained. Through analytic determination of the product, the molecule weight are 2793 g/mol, 3038 g/mol, the molecule weight distribution are 1.105, 1.095, the conversion rate are 95%, 93%, the selectivity for sulfydryl are 94%, 95%.

Embodiment 8. Employing the Immobilized Enzyme Micro Reactor for Synthetizing the Mercapto Functional Poly (δ-Valerolactone)

Filling 1.18 g immobilized enzyme Novozyme435 into the micro channel, which is rinsed by the toluene after re-steaming dehydration to remove the air and water in the device. Adding 4.0048 g ε-caprolactone, 0.5370 g/0.1074 g/0.06712 g/0.05370 g mercapto hexanol and 5.3 ml toluene solution into an ampoule bottle after dehydration under 500° high temperature and air exchanging for three times, transferring into a injector after shaking evenly, controlling the flow rate as 0.6033 mL/min, 0.0362 mL/min, 0.03017 mL/min, 0.01508 mL/min respectively, then inputting the mixed solution into the immobilized enzyme micro reaction channel for polymerization under 60°, a poly (ε-caprolactone) reaction solution of 2 ml is collected after stable reaction (reaction solution of about 5 ml is discarded). Adding 80 ml methanol and putting into a refrigerator with −30° C. for 4 h, then collecting the precipitation by filtering and putting into a vacuum drying chamber for 24 h after natural-air drying the precipitation, and a purified poly (δ-valerolactone) may be obtained. Through analytic determination of the product, the molecule weight are 1035 g/mol, 5090 g/mol, 8200 g/mol, 9900 g/mol, the molecule weight distribution are 1.029, 1.065, 1.106, 1.165, the conversion rate are 94%, 93%, 94%, 95%, the selectivity for sulfydryl are 93%, 96%, 95%, 96%.

Embodiment 9. Employing the Immobilized Enzyme Micro Reactor for Synthetizing the Mercapto Functional Poly (δ-Valerolactone)

Filling 1.18 g immobilized enzyme Novozyme435 into the micro channel, which is rinsed by the toluene after re-steaming dehydration to remove the air and water in the device. Adding 6.0072 g δ-valerolactone, 0.2685 g 6-mercapto-1-hexanol and 9.29 ml tetrahydrofuran/dichloromethane solvent into an ampoule bottle after dehydration under 500° high temperature and air exchanging for three times, transferring into a injector after shaking evenly, controlling the flow rate as 0.362 mL/min, then inputting the mixed solution into the immobilized enzyme micro reaction channel for polymerization under 60°, a poly (δ-valerolactone) reaction solution of 8 mins (about 2 ml) is collected after stable reaction of about 14 mins. Adding 80 ml methanol and putting into a refrigerator with −30° C. for 4 h, then collecting the precipitation by filtering and putting into a vacuum drying chamber for 24 h after natural-air drying the precipitation, and a purified poly (δ-valerolactone) may be obtained. Through analytic determination of the product, the molecule weight are 3090 g/mol, 3135 g/mol, the molecule weight distribution are 1.181, 1.154, the conversion rate are 94%, 95%, the selectivity for sulfydryl are 94%, 92%.

Embodiment 10. Employing the Immobilized Enzyme Micro Reactor for Synthetizing the Mercapto Functional Poly (δ-Valerolactone)

Filling 1.18 g immobilized enzyme Novozyme435 into the micro channel, which is rinsed by the toluene after re-steaming dehydration to remove the air and water in the device. Adding 6.0072 g δ-valerolactone, 0.1563 g 2-mercaptoethanol/0.1843 g 3-mercapto-1-propanol/0.2124 g 4-mercapto-1-butanol and 5.3 ml toluene solvent into an ampoule bottle after dehydration under 500° high temperature and air exchanging for three times, transferring into a injector after shaking evenly, controlling the flow rate as 0.362 mL/min, then inputting the mixed solution into the immobilized enzyme micro reaction channel for polymerization under 60°, a poly (ε-caprolactone) reaction solution of 2 ml is collected after stable reaction (reaction solution of about 5 ml is discarded). Adding 80 ml methanol and putting into a refrigerator with −30° C. for 4 h, then collecting the precipitation by filtering and putting into a vacuum drying chamber for 24 h after natural-air drying the precipitation, and a purified poly (ε-caprolactone) may be obtained. Through GPC determination of the product, the molecule weight are 3143 g/mol, 3200 g/mol, 3254 g/mol, the molecule weight distribution are 1.152, 1.092, 1.132, the conversion rate are 93%, 95%, 92%, the selectivity for sulfydryl are 93%, 96%, 94%.

Embodiment 11. Employing the Immobilized Enzyme Micro Reactor for Synthetizing the Mercapto Functional Poly (ε-Caprolactone), and Testing the Reusability of the Immobilized Enzyme Filling 1.18 g immobilized enzyme Novozyme435 into the micro channel, which is rinsed by the toluene after re-steaming dehydration to remove the air and water in the device. Adding 68.484 g ε-caprolactone, 2.6848 g 6-mercapto-1-hexanol and 80.77 ml toluene solution into an ampoule bottle after dehydration under 500° C. high temperature and air exchanging for three times, transferring into a injector after shaking evenly, controlling the flow rate as 0.362 mL/min (reaction time as 5 mins), then inputting the mixed solution into the immobilized enzyme micro reaction channel for polymerization under 60° C. a poly (ε-caprolactone) reaction solution (about 2 ml) is collected every 5 mins after stable reaction of about 14 mins. Measuring the conversion rate of 0.1 ml reaction solution of nuclear magnetically, and then adding 80 ml methanol and putting into a refrigerator with −30° C. for 4 h, collecting the precipitation by filtering and putting into a vacuum drying chamber for 24 h after natural-air drying the precipitation, and a purified poly (ε-caprolactone) may be obtained. The molecule weight and molecule weight distribution of the product is determined by GPC. The result shows that the poly (ε-caprolactone) molecule weight remains constant as 3200~3600 g/mol, the molecule weight distribution is 1.01~1.15, the conversion rate is larger than 90%, the selectivity for sulfydryl is larger than 90% after the reaction experiencing 74 circulations, the reusability of immobilized enzyme in the micro reactor is increased greatly in comparison with in the traditional autoclavereactor.

Figure 2:
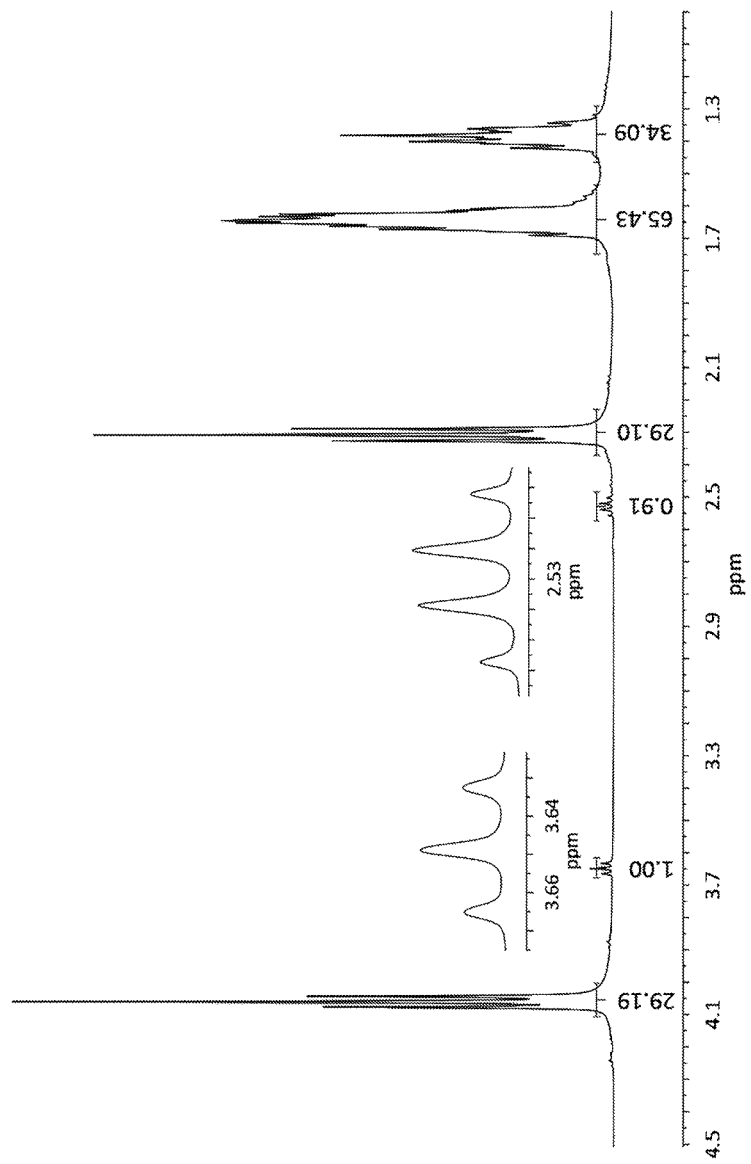
FIG. 2 is a $^1$H NMR detection diagram of the product in the embodiment 11.

In order to define final product, the result of $^1$H NMR detection on the final product obtained in the embodiment 1 by the inventors shows that the final product is poly (ε-caprolactone) and the selectivity for sulfydryl is larger than 90%. Results of $^1$H NMR detection are shown in FIG. 2

What is claimed is:

1. A method for preparing polyester polyol by using a micro-reaction device, wherein the micro-reaction device comprising a feed inlet, a micro mixer and a micro reactor connected in turn via a connecting tube;
the method comprising the follow steps
    (1) dissolving a lactone monomer into a first organic solution;
    (2) dissolving a mercapto alcohol into a second organic solution;
    (3) mixing the solution in step (1) with the solution in step (2) into a homogeneous mixture, and pumping the homogeneous mixture into the micro-reaction device for reacting for a sufficient amount of time to produce the polyester polyol compound where the micro-reactor comprises an immobilized enzyme; and
    (4) recovering and purifying the polyester polyol;
    wherein the lactone is a δ-valerolactone) or ε-caprolactone; the polyester polyol is a mercapto functional poly (δ-valerolactone) or a mercapto functional poly (ε-caprolactone).

2. The method according to claim 1, characterized in that, in the step (1), the lactone monomer is ε-caprolactone or δ-valerolactone, the organic solution is toluene, a tetrahydrofuran or a dichloromethane; wherein, the concentration of the lactone monomer in the mixed system acquired in the step (1) is 1-6 mol/L.

3. The method according to claim 1, characterized in that, in the step (2), the mercapto alcohol is a 2-mercaptoethanol, a 3-mercapto-1-propanol, 4-mercapto-1-butanol or a 6-mercapto-1-hexanol, the organic solution is toluene, tetrahydrofuran or dichloromethane; wherein, the concentration of the mercapto alcohol in the mixed system acquired in step (2) is 0.01-0.6 mol/L.

4. The method according to claim 1, characterized in that in step (3), the reaction temperature in the micro reactor is 40-140° C., and the duration of stay is 1-180 mins.

5. The method according to claim 1, characterized in that the immobilized enzyme in step (3) is the immobilized lipase Novozyme435.

6. The method according to claim 1, characterized in that, in step (3), the method for separation and purification is: adding methanol or hexanol or other solvent, which is soluble for monomer and mercapto-alcohol but non-soluble for the result functional polyester polyol, into the product acquired from the reaction, and precipitating them, then vacuum drying the solid portion obtained by filtering to acquire the product.

7. The method according to claim 1, characterized in that the molar ratio of the lactone monomer and the mercapto alcohol is 5-100:1.

8. The method according to claim 1, characterized in that, the mass ratio of the immobilized enzyme and the lactone monomer is 1:3-20.

* * * * *